(12) United States Patent
Biedermann et al.

(10) Patent No.: US 8,123,784 B2
(45) Date of Patent: Feb. 28, 2012

(54) ANCHORING ELEMENT FOR USE IN SPINE OR BONE SURGERY, METHODS FOR USE AND PRODUCTION THEREOF

(75) Inventors: Lutz Biedermann, VS-Villingen (DE); Jürgen Harms, Karlsruhe (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 10/799,143

(22) Filed: Mar. 11, 2004

(65) Prior Publication Data

US 2004/0181224 A1    Sep. 16, 2004

(30) Foreign Application Priority Data

Mar. 11, 2003  (DE) .................. 103 10 540

(51) Int. Cl.
*A61B 17/70*    (2006.01)
(52) U.S. Cl. ..................................... 606/264
(58) Field of Classification Search .......... 606/61; 605/61
See application file for complete search history.

(56) References Cited

U.S. PATENT DOCUMENTS

| | | | | |
|---|---|---|---|---|
| 4,041,939 A * | 8/1977 | Hall | ........... | 606/61 |
| 4,763,644 A | 8/1988 | Webb | ........... | 128/69 |
| 5,005,562 A | 4/1991 | Cotrel | | |
| 5,129,900 A | 7/1992 | Asher et al. | | |
| 5,190,543 A | 3/1993 | Schläpfer | | |
| 5,217,497 A | 6/1993 | Mehdian | | |
| 5,443,467 A | 8/1995 | Biedermann et al. | | |

(Continued)

FOREIGN PATENT DOCUMENTS

DE    43 07 576 C1    4/1994

(Continued)

OTHER PUBLICATIONS

Product information for Medtronic Sofamor Danek; CD Horizon Legacy 5.5 Spinal System dated 2003.

(Continued)

*Primary Examiner* — Eduardo C Robert
*Assistant Examiner* — Mary Hoffman
(74) *Attorney, Agent, or Firm* — Christie, Parker & Hale LLP

(57) ABSTRACT

An anchoring element for use in spinal or bone surgery is described. A shaft (1) for anchoring in a vertebra or bone section is connected to a receiving part (22) which serves to connect to a rod (100) having a pre-determined diameter (D). The receiving part (22) provides a U-shaped recess (26) forming a channel for the reception of the rod and two legs (27, 28). The legs are free on their end and have a thread (30, 31) that cooperates with a securing element to fix the rod in the receiving part. When inserted into the receiving part, the rod surface facing the end surface (29) is at a pre-determined distance (A) in an axial direction from the end surface (29). The thread (30, 31) of the legs extends from the end surface a distance that is smaller than or equal to the pre-determined distance (A). Also, an undercut (33, 34) is provided adjacent to the thread whose edge farthest away from the thread is located at a distance (B) from the end surface. Distance (B) is larger than the pre-determined distance (A). The anchoring element is cheap to manufacture and has a reduced overall height as compared to the known anchoring elements. Methods of using the anchoring element also are described.

20 Claims, 2 Drawing Sheets

U.S. PATENT DOCUMENTS

| | | | |
|---|---|---|---|
| 5,474,555 A | 12/1995 | Puno et al. | |
| 5,554,157 A | 9/1996 | Errico et al. | 606/61 |
| 5,725,527 A * | 3/1998 | Biedermann et al. | 606/61 |
| 5,810,818 A | 9/1998 | Errico et al. | 606/61 |
| 5,817,094 A | 10/1998 | Errico et al. | 606/61 |
| 5,873,878 A * | 2/1999 | Harms et al. | 606/61 |
| 6,224,596 B1 * | 5/2001 | Jackson | 606/61 |
| 6,231,575 B1 | 5/2001 | Krag | |
| 6,485,491 B1 | 11/2002 | Farris et al. | 606/61 |
| 2003/0023243 A1 | 1/2003 | Biedermann et al. | |
| 2003/0100896 A1 | 5/2003 | Biedermann et al. | |
| 2004/0186473 A1 | 9/2004 | Cournoyer et al. | |

FOREIGN PATENT DOCUMENTS

| | | |
|---|---|---|
| DE | 299 03 342 U1 | 2/1999 |
| DE | 298 10 798 U1 | 10/1999 |
| DE | 101 36 129 A1 | 2/2003 |
| DE | 101 57 969 C1 | 2/2003 |
| JP | 2000-102544 | 4/2000 |
| JP | 2001-276086 | 10/2001 |

OTHER PUBLICATIONS

Walker, John R., *Machining Fundamentals—Fundamentals Basic to Industry,* 1981, pp. 2, 179-186, The Goodheart-Wilcox Co., Inc., South Holland, Illinois.

Lascoe et al. *Machineshop—Operations and Setups,* 1973, pp. 380, 386, and 388, 4th Edition, American Technical Society, Chicago.

Opinion, 05-1415, Mar. 20, 2007, U.S. Court of Appeals for the Federal Circuit, *Cross Medical Products, Inc. v. Medtronic Sofamor Danek, Inc.*

English translation of German Patent DE 298 10 798, Jul. 12, 2007 Office action.

Patent Abstracts of Japan, JP 2001-276086, Oct. 9, 2001, Eiji et al.

English translation of Office action for corresponding Japanese application 066066/2004, mailed Oct. 20, 2009, 2 sheets.

* cited by examiner

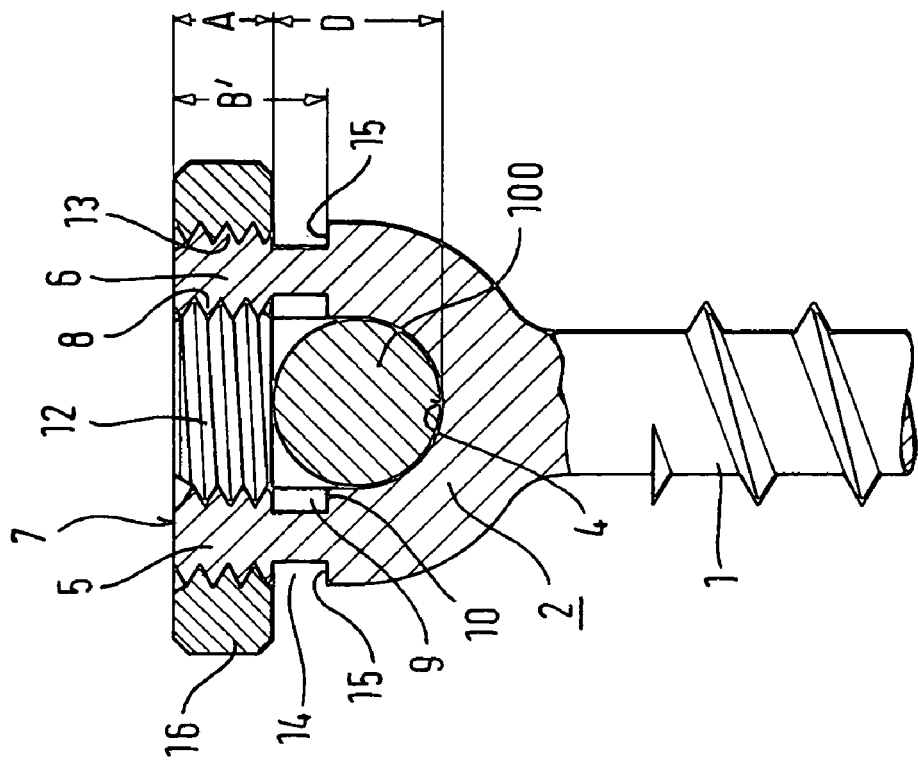
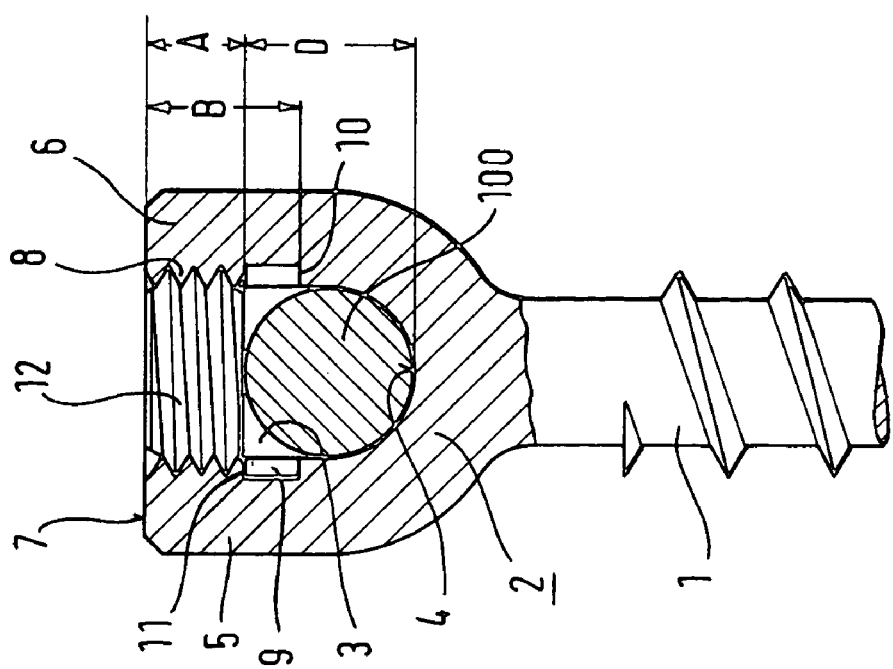

ANCHORING ELEMENT FOR USE IN SPINE OR BONE SURGERY, METHODS FOR USE AND PRODUCTION THEREOF

FIELD OF THE INVENTION

The present invention relates to an anchoring element for use in spinal or bone surgery and to methods for the manufacture and use thereof. The anchoring element typically has (i) a shaft for anchoring in a vertebra or bone section, (ii) an essentially cylindrical receiving part which is connected to the shaft and serves to connect to a rod of a pre-determined diameter (D), and (iii) a securing element comprising a thread. The receiving part comprises an U-shaped recess with a channel for the reception of the rod and forming two legs which are free on their ends. The legs comprise a thread for cooperating with the securing element.

BACKGROUND OF THE INVENTION

An anchoring element in the form of a monoaxial bone screw is described in U.S. Pat. No. 5,005,562 and in the form of a polyaxial bone screw is described in DE 43 07 576 C1. Typically such anchoring elements comprise a receiving part for the reception of a rod connecting several anchoring elements of this type, a bone anchoring screw element that is monoaxially or polyaxially connected to the receiving part, and an internal screw that is to be screwed in between the legs of the receiving part and serves for the fixation of the rod. The receiving part according to DE 43 07 576 C1 further comprises an external screw nut that can be screwed onto the receiving part for additional fixation.

In such anchoring elements, the internal thread or external thread of the receiving part has incorporated a thread runout. Further, the distance between the rod support within the receiving part and the thread runout is smaller than the diameter of the rod to be received. This ensures that the internal screw or the external screw nut can exert a sufficient clamping force on the rod.

For a given rod diameter, the length of the free legs of the receiving part and, thus, the overall height of the anchoring element from the rod support generally is determined by the distance over which the internal and/or external thread is provided to ensure reliable fixation. In the area of the thread runout, which may include more than one thread tooth, the depth of the thread diminishes and the profile of the thread tooth is poorly defined. In order to provide for sufficiently firm attachment of the internal screw or external screw nut, it must be ensured that a sufficient number of turns of thread with a deep profile are present. Therefore, it is necessary either to place the thread runout sufficiently far down in the direction of the rod support or a corresponding number of turns of thread with a deep profile must be provided upwards in the direction of the free end of the legs which increases the overall height.

Moreover, the manufacture of the thread with a thread runout is resource-consuming from the point of view of manufacturing technology.

Thus, it is desirable to have an improved anchoring element of the type described above which is easy to manufacture and has a reduced overall height, but provides the same degree of safety against the rod becoming loose as is provided by the conventional anchoring elements.

SUMMARY OF THE INVENTION

The present invention provides an anchoring element along with a method for manufacturing the same. In accord with the present invention, an anchoring element for use with a rod having a pre-determined diameter (D) in spinal or bone surgery comprises a shaft for anchoring in a vertebra or bone section, a receiving part with a longitudinal axis which is connected to the shaft and serves to connect to the rod, the receiving part comprising a U-shaped recess forming a channel for the reception of the rod and two legs each having a free end, the two legs further having a first thread, and a securing element comprising a second thread that cooperates with the first thread, wherein the legs have a length such that, when the rod is inserted in the recess, a surface of the rod facing the free end is at a pre-determined distance (A) from the free ends in an axial direction, wherein the first thread, when viewed from the free end of a leg, extends from the free end to a distance that is smaller than or equal to the pre-determined distance (A), the receiving part further comprising an undercut adjacent to the first thread having an edge farthest away from the first thread at a distance (B) from the free end, the distance (B) being larger than the pre-determined distance (A).

Preferably, the anchoring element is manufactured such that the undercut is provided in the receiving part before the first thread is provided therein.

In certain embodiments of the invention, the depth of the undercut corresponds to the depth of the thread.

In various embodiments of the invention the first thread is an internal thread and the securing element is implemented as an internal screw. Alternatively, the first thread can be an external thread and the securing element can be implemented as a screw nut. The first thread can take any known form, for example, it can be implemented as a metric thread, buttress thread, flat thread or as a thread with a negative load-bearing angle.

In certain embodiments of the invention, the connection between the shaft and the receiving part is implemented to be monoaxial. In other embodiments, the connection between the shaft and the receiving part is implemented to be polyaxial.

The new anchoring element described herein is advantageous in that it is cheaper to manufacture, because the cutting of the thread in the receiver part in accordance with the present invention is less resource-consuming from the point of view of manufacturing technology. Moreover, the height of the receiving part of the anchoring element of the invention is reduced from conventional receiving parts having the poorly defined runout thread teeth.

The invention also provides a method for performing spinal or bone surgery, the method comprising providing a bone anchoring element as described above, screwing the shaft into a vertebra or bone section, positioning a rod into the U-shaped recess and fixing the rod in the bone anchoring element with the securing element. Preferably, a plurality of bone anchoring elements are positioned into various sites of a vertebra or bone section, and the rod is fixed into the plurality of anchoring elements. When a polyaxial bone anchoring element is used, the method also includes adjusting the angular orientation of the receiving part relative to the screw member.

Additional features and characteristics of the present invention are evident from the description of embodiments in view of the drawings.

BRIEF DESCRIPTION OF THE DRAWINGS

FIG. 1 shows a side view partially in section of the upper portion of one embodiment of an anchoring element in accord with the present invention;

FIG. 2 shows a side view partially in section of the upper portion of a second embodiment of an anchoring element in accord with the present invention.

DETAILED DESCRIPTION OF THE INVENTION

Figure 3:
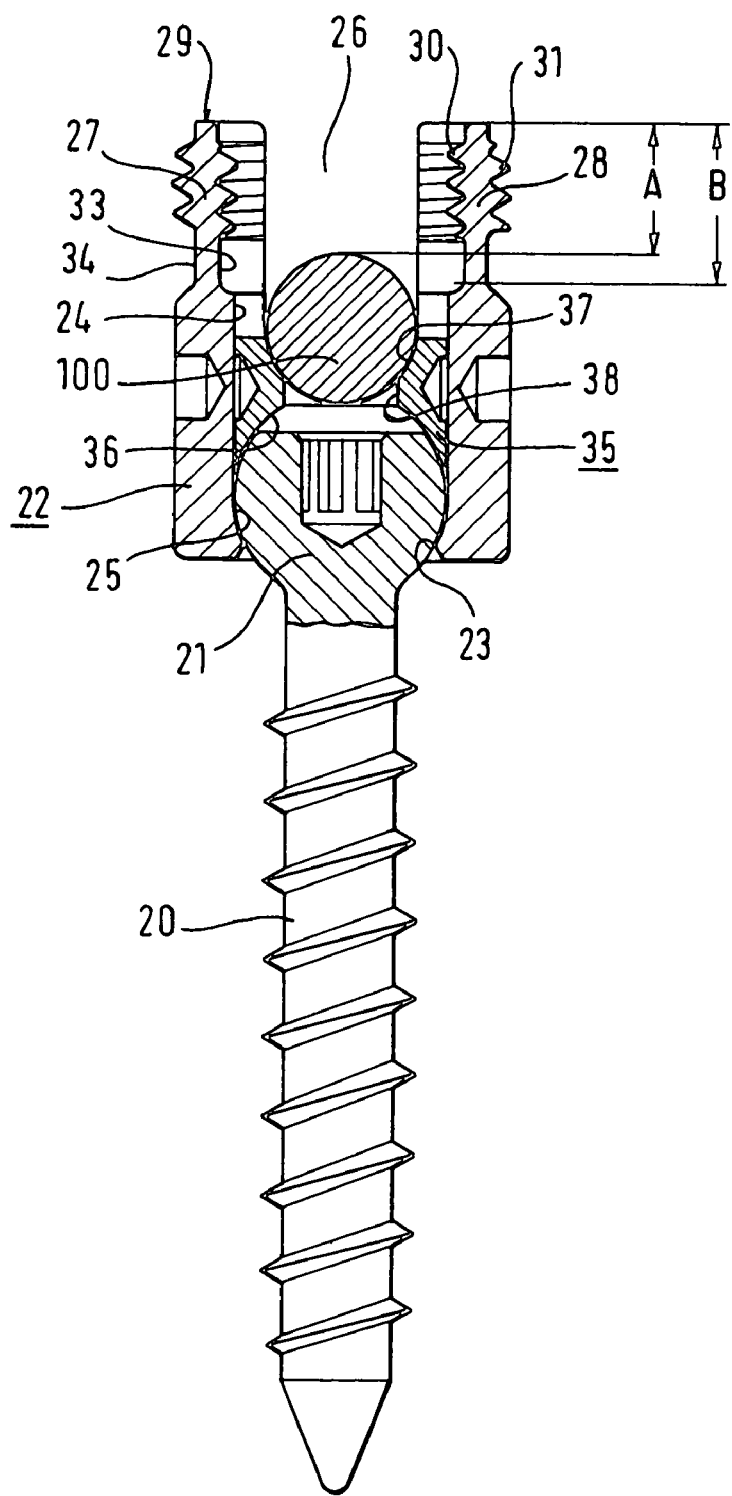
FIG. 3 shows a side view partially in section of a third embodiment of an anchoring element in accord with the present invention.

A monoaxial bone screw is illustrated in FIG. 1 as a first embodiment of a bone anchoring element in accord with the present invention. The bone screw comprises a shaft 1 with a bone thread section and an essentially cylindrical receiving part 2 which is rigidly connected to the shaft and serves to receive a rod 100 of a given diameter D which connects the bone screw to additional bone screws. For this purpose, the receiving part 2 comprises a recess 3 forming a channel having a U-shaped cross section. The recess is dimensioned just large enough for rod 100 to be inserted and held by the channel formed by the base 4 of the recess and its side walls. The U-shaped recess 3 forms two legs 5, 6 which extend from the base 4 forming the side walls and having free ends that form the upper end 7 of the receiving part. When the rod is inserted into the channel and abuts on base 4 of the U-shaped recess, the topmost surface of the rod is at a pre-determined distance A from the upper end 7 of the receiving part.

An internal thread 8 extends from the upper end 7 along legs 5, 6 over a distance, which is equal to the pre-determined distance A, as illustrated in FIG. 1. In the embodiment shown, the internal thread is provided as a metric thread. On the inner surface of the legs 5, 6 adjacent to the internal thread is a recess or an undercut 9 which extends in a circumferential direction. The lower edge 10 of the undercut 9 farthest away from the thread 8 is located at a distance B from upper end 7. The distance B is larger than the pre-determined distance A. Thus, the lower edge 10 of the undercut 9 is located at a distance from base 4 of the recess that is smaller than the rod diameter D. In the embodiment shown, the upper edge 11 of the undercut closest to the upper end 7 resides at the level of the rod topmost surface and, thus, is located at a distance A from the free end. It is preferred that the depth of the undercut at least be equal to the depth of thread 8. The cross-section of undercut 9 is formed to be essentially rectangular.

A securing element in the form of an internal screw 12 with an outer thread engaging and cooperating with the internal thread is provided for the fixation of the rod in the receiving part.

In operation, the bone screw is screwed into the bone first followed by the insertion of the rod. Subsequently, the internal screw 11 is screwed in until its bottom side facing the rod presses onto the rod and fixes the rod in its position. The manufacture of the bone screw preferably proceeds such that the undercut 9 in the receiving part is produced in a first step of the procedure and the thread 8 is produced in a second step of the procedure. The manufacturing process for making this anchoring element involves a smaller number of turns of thread as compared to the conventional anchoring elements with thread runout. In contrast, these fewer turns of thread possess a well-defined profile and, thus, high load-bearing capacity. Consequently, the entire thread 8 can be shifted downwards in the direction of base 4 by the length of the weak runout thread teeth present in conventional anchoring elements with thread runout. As a result, the overall height of the receiving part is reduced as compared to the conventional anchoring elements. Moreover, the manufacture is cheaper, because the cutting of the thread is less work-intensive due to elimination of the thread runout.

Alternatively, the internal thread 8 extends from the upper end 7 over a distance that is smaller than the pre-determined distance A, such that the upper edge 11 of the undercut 9 is located above the rod topmost surface when viewed in direction to the upper end 7, when the rod 100 is positioned in the recess 3. Modifications of the geometry of the undercut 9 can be made by those skilled in the art without departing from the spirit of the invention. For example, the undercut 9 can be formed to have rounded corners or the upper and lower edge of the undercut can be beveled.

The thread also can be provided in alternative forms. For example, the internal thread can be provided in the form of a buttress thread or saw teeth thread and, particularly, in the form of a buttress thread with a horizontal load-bearing flank, or in the form of a flat thread with two horizontal flanks, or in the form of a thread with a negative load-bearing flank angle rather than in the form of a metric thread. In any case, the internal screw 12 comprises a corresponding external thread for cooperation with the internal thread 8. Further, the threads can be provided in the form of right-hand or left-hand threads.

In the embodiment shown in FIG. 2, an additional external thread 13 is provided on the legs 5, 6. Preferably, the external thread 13 extends to a pre-determined distance from the upper end 7 at least equal to distance A of the rod topmost surface, as shown. Also, preferably, undercut 14 is provided adjacent to the external thread 13, with the lower edge 15 of said undercut, closest to base 4, located at a distance B' from the upper end 7, wherein B' is larger than the pre-determined distance A. Preferably, the depth of the undercut at least is equal to the depth of the external thread. In this embodiment, an additional securing element is provided in the form of an external screw nut 16 which comprises an internal thread that engages and cooperates with the external thread 13.

The operation of this embodiment is similar to that of the first embodiment except for the additional step, in which the external screw nut is screwed on as an additional securing element.

Compared to the first embodiment, the manufacture of the anchoring element of this embodiment includes the additional steps of forming the external undercut 14 and the external thread 13. As in the previously described procedure for the internal undercut and thread, preferably, the undercut is provided first and the external thread, subsequently.

Alternatively, the distance for which the internal thread 8 is provided on legs 5, 6 can differ from the distance for which the external thread 13 is provided. It is very important for making anchoring elements that properly incorporate the teachings of this invention that neither the internal thread nor the external thread extend from the upper end 7 further than to the level of the rod topmost surface and that the lower edge of the undercut 9 or 13 is positioned always below the rod topmost surface. However, other dimensions such as, for example, the heights (i.e., length along the longitudinal axis) and depths of the undercuts may vary.

In a further embodiment of the invention, the receiving part of the anchoring element has no internal thread or adjacent internal undercut and an internal screw is not used as the securing element. Instead, in this embodiment, there is only an external thread and an adjacent external undercut provided. The rod is secured using an external cap and a pressure element, which may be part of or separate from the cap.

As an alternative to the embodiment illustrated in FIG. 2, an undercut can be provided adjacent to only one of the two threads, i.e., either the internal thread or the external thread.

It should be understood that all modifications described herein are applicable to the embodiment of the invention having suitable structure for the modification.

An embodiment illustrating the use of a polyaxial bone screw for an anchoring element in accord with the present invention is illustrated in FIG. 3. The polyaxial bone anchoring element comprises a screw element having a shaft 20 with a bone thread and a spherical segment-shaped head 21, which is connected to a receiving part 22. On one of its ends, receiving part 22 is provided with a first bore 23 in an axially symmetrical alignment, whose diameter is larger than that of the thread section of thread shaft 20 and smaller than that of head 21. Moreover, receiving part 22 is provided with a coaxial second bore 24 which is open on its end opposite from the first bore 23 and whose diameter is sufficiently large for the thread shaft of the screw element to be guided through the first bore 23 and for the head 21 to be guided through to the base of the first bore 23. A small coaxial section 25 is provided between the first bore and the second bore, said small coaxial section 25 being adjacent to the first bore 23 and being of spherical shape to receive and cooperate with the spherical segment-shaped head 21 of the screw element.

Receiving part 22 further comprises a U-shaped recess 26 which is arranged symmetrically with regard to the longitudinal axis of the receiving part and serves for the insertion of the rod 100. The base of the recess 26 is directed towards the first bore 23 and the recess forms two free legs 27, 28, whose ends form the upper end 29 of the receiving part.

An internal thread 30 and, preferably, an external thread 31 are provided on legs 27, 28 adjacent to the upper end 29 with the threads extending over a pre-determined distance from upper end 29. Moreover, adjacent to the internal thread 30 and to the external thread 31 there are provided undercuts 33, 34 on the side of the thread facing away from the upper end 29.

A cylindrical pressure element 35 is provided whose outer diameter is selected such that the pressure element can be inserted in the receiving part from the upper end 29 positioned within bore 24 adjacent the head 21. The end of the pressure element facing head 21 comprises a spherical segment-shaped recess 36 which widens towards that end and whose spherical radius is selected to cooperate with head 21 such that the pressure element surrounds head 21 from above when it is inserted in the receiving part and can fix the head 21 to achieve a desired angular position of the shaft 20 relative to the longitudinal axis of the receiving part. The opposite end of the pressure element comprises a U-shaped recess 37 whose dimensions are such that the rod 100 can be inserted and is held therein. When the pressure element 35 is inserted into the receiving part 22, the U-shaped recess 37 of pressure element 35 forms a channel having a base in which the rod is supported. In the embodiment shown, the side walls of the U-shaped recess 37 of the pressure element do not protrude beyond the inserted rod. Moreover, the pressure element has a central bore 38 through which a screwing tool can be inserted to allow the screw element to be screwed in. Thus, the screw element can be pre-assembled with the receiving part 22 and pressure element 35 loosely holding the screw element therein.

An internal screw pressure member is provided for the fixation of both the head in its angular position and the rod in the recess 37. Turning the internal screw pressure element into the recess 37 until it exerts pressure on the topmost surface of the rod fixes the rod and transmits pressure through the rod to pressure element 35 to fix the orientation of head 21. Preferably, an external screw nut also is provided for additional fixation.

In the assembled state of the anchoring element with the rod inserted and pressure element 35 pressing on the head 21, the topmost surface of the rod resides at a distance A from upper end 29 of the receiving part. In the embodiment shown, the internal thread 30 and the external thread 31 are dimensioned such that they extend from the upper end 29 to a distance that is smaller than distance A. The lower edge of the undercuts 33, 34 closest to the base of the U-shaped recess 37 of pressure element 35 are located at a distance B from upper end 29 that is larger than distance A between the rod topmost surface and the upper end.

In operation, the screw element is inserted in the receiving part in known fashion, then, the internal pressure screw member is inserted and the screw is screwed into the bone. Thus, the screw element and receiving part can be conveniently pre-assembled prior to screwing the bone screw element into the bone. Subsequently, the rod is inserted, the angular arrangement of the receiving part with respect to the screw element is adjusted, and the rod is positioned and, then, the angular arrangement and the rod are fixed by screwing in the internal pressure screw member. Finally, the external screw nut is applied in known fashion.

The manufacture of this anchoring element, with regard to the cutting of the threads and undercuts of the receiving part, is identical to the procedure of the embodiments described previously.

As stated above, the internal thread and external thread can differ and vary in length and/or the undercuts can differ and vary in depth and height. Again, all modifications or alternatives described previously are equally applicable to this polyaxial embodiment.

The manufacture of the anchoring element of this embodiment proceeds such that the undercuts 33, 34 in the receiving part are produced first and the corresponding threads 30, 31 are produced in a subsequent step of the procedure. As with the monoaxial embodiments, the manufacturing process for making this anchoring element involves a smaller number of turns of thread as compared to the conventional anchoring elements with thread runout. In contrast, these fewer turns of thread possess a well-defined profile and, thus, high load-bearing capacity. Consequently, the overall height of the receiving part is reduced as compared to the conventional anchoring elements. Moreover, the manufacture is cheaper, because the cutting of the thread is less work-intensive due to elimination of the thread runout.

The invention has been described in detail including the preferred embodiments thereof. However, it will be appreciated that those skilled in the art, upon consideration of the description and drawings, may make modifications and improvements within the spirit and scope of the invention.

What is claimed is:

1. An anchoring element for use in spinal or bone surgery; said anchoring element comprising:
    a shaft for anchoring to a vertebra or a bone section;
    a rod for connecting to the shaft, the rod having a pre-determined diameter (D) and an outer surface;
    a receiving part that is structured and arranged to connect the rod to the shaft, the receiving part having a longitudinal axis and comprising a U-shaped recess forming a channel for the reception of the rod and two legs having free ends, the legs comprising a first internal thread, the legs further providing an exterior end surface of the receiving part; and
    a securing element comprising a screw member having a first external thread that engages and cooperates with the first internal thread to result in contact between the securing element and the rod to fix the rod in its position in the channel of the receiving part;
    wherein, when the rod is located in the channel, a first distance from the exterior end surface of the receiving part to a closest portion of the outer surface of the rod in an axial direction is a pre-determined distance (A), the first internal thread extending from a first location at or adjacent the exterior end surface of the receiving part to a second location that is a second distance from the exterior end surface that is smaller than or equal to the pre-determined distance (A); and wherein the receiving part further comprising an undercut on an inner surface of the legs adjacent to the first internal thread, the undercut extends in a circumferential direction and the first internal thread extending to the undercut, the undercut having an edge farthest away from the first internal thread, the edge being located at a third distance (B) from the exterior end surface, the distance (B) being larger than the predetermined distance (A);

wherein the first external thread of the securing element is movable into the undercut;

wherein an entire length of the securing element in the axial direction is equal to or less than the predetermined distance (A).

2. The anchoring element according to claim 1, wherein the undercut has a depth that corresponds at least to a depth of the first internal thread.

3. The anchoring element according to claim 1, further comprising a screw nut having an internal thread; and wherein the receiving part further comprises an external thread that cooperates with the internal thread of the screw nut.

4. The anchoring element according to claim 1, wherein a connection between the shaft and the receiving part is structured and arranged to be a monoaxial connection.

5. The anchoring element according to claim 1, wherein the shaft and the receiving part are an integral part.

6. The anchoring element according to claim 1, wherein a connection between the shaft and the receiving part is structured and arranged to be a polyaxial connection.

7. The anchoring element according to claim 1, wherein one of the first internal thread of the receiving part and the first external thread of the securing element comprises fewer than four full turns.

8. The anchoring element according to claim 7 wherein the securing element fixes the rod in the receiving part without protruding outward beyond the exterior end surface of the receiving part.

9. The anchoring element according to claim 7, wherein the securing element is a monolithic securing element and threading of the first external thread of the securing element to the first internal thread of the receiving part results in contact between the securing element and a portion of the rod located between the two legs of the receiving part to fix the rod in its position in the channel of the receiving part.

10. The anchoring element according to claim 1, wherein both of the first internal thread of the receiving part and the first external thread of the securing element comprises fewer than four full turns.

11. The anchoring element according to claim 10 wherein the securing element fixes the rod in the receiving part without protruding outward beyond the exterior end surface of the receiving part.

12. The anchoring element according to claim 10, wherein the securing element is a monolithic securing element and threading of the first external thread of the securing element to the first internal thread of the receiving part results in contact between the securing element and a portion of the rod located between the two legs of the receiving part to fix the rod in its position in the channel of the receiving part.

13. The anchoring element of claim 1, wherein the undercut comprises a partial cylindrical surface having a cylinder axis that extends in the same direction as the longitudinal axis.

14. The anchoring element of claim 10, wherein the undercut comprises a partial cylindrical surface around the longitudinal axis.

15. An anchoring element for use in spinal or bone surgery; said anchoring element comprising:

a screw member comprising a spherical segment-shaped head and a shaft with a bone thread;

a rod for connecting to the shaft, the rod having a predetermined diameter (D) and an outer surface;

a receiving part that is structured and arranged to connect the rod to the shaft, the receiving part comprising a longitudinal axis, a first bore in axial alignment therewith and having a first diameter of sufficient size to permit the bone thread of the shaft to pass through but not to permit the head to pass through, and a second bore coaxial with the first bore and having a second diameter of sufficient size to permit the head to pass through, the receiving part further comprising a U-shaped recess forming a channel for the reception of the rod and two legs having free ends, the legs comprising a first internal thread, the legs further providing an exterior end surface of the receiving part;

a cylindrical pressure element having an outer diameter of a size capable of being inserted into the receiving part and having a first side shaped to engage the head of the screw element and a second side opposite the first side shaped to receive the rod inserted into the U-shaped recess; and a securing element comprising a first external thread that engages and cooperates with the first internal thread to result in contact between the securing element and the rod to fix the rod in its position in the channel of the receiving part;

wherein, when the rod is located in the channel, a first distance from the exterior end surface of the receiving part to a closest portion of the outer surface of the rod in an axial direction is a pre-determined distance (A), the first internal thread extends from a first location at or adjacent the exterior end surface of the receiving part to a second location that is a second distance from the exterior end surface that is smaller than or equal to the pre-determined distance (A); and wherein the receiving part further comprising an undercut on an inner surface of the legs adjacent to the first internal thread, the undercut extends in a circumferential direction and the first internal thread extending to the undercut, the undercut having an edge farthest away from the first internal thread, the edge being located at a third distance (B) from the exterior end surface, the distance (B) being larger than the predetermined distance (A);

wherein the first external thread of the securing element is movable into the undercut;

wherein an entire length of the securing element in the axial direction is equal to or less than the predetermined distance (A).

16. The anchoring element according to claim 15, wherein the undercut has a depth that corresponds at least to the depth of the first internal thread.

17. The anchoring element according to claim 15, further comprising a screw nut having an internal thread;

wherein the receiving part further comprises an external thread that cooperates with the internal thread of the screw nut.

18. The anchoring element according to claim 15, wherein the threads each are a thread selected from a metric thread, a buttress thread, a flat thread or a thread with a negative load-bearing angle.

19. An anchoring element for use in spinal or bone surgery; said anchoring element comprising:
   a shaft for anchoring to a vertebra or a bone section;
   a rod for connecting to the shaft, the rod having a pre-determined diameter (D) and an outer surface;
   a receiving part that is structured and arranged to connect the rod to the shaft, the receiving part having a longitudinal axis and comprising a U-shaped recess forming a channel for the reception of the rod and two legs having free ends, the legs comprising a first internal thread, the legs further providing an exterior end surface of the receiving part; and
   a monolithic securing element comprising a screw member having a first external thread comprising fewer than four full turns and wherein threading of the first external thread of the securing element to the first internal thread of the receiving part results in contact between the securing element and a portion of the rod located between the two legs of the receiving part to fix the rod in its position in the channel of the receiving part;
   wherein, when the rod is located in the channel, a first distance from the exterior end surface of the receiving part to a closest portion of the outer surface of the rod in an axial direction is a pre-determined distance (A), the first internal thread extending from a first location at or adjacent the exterior end surface of the receiving part to a second location that is a second distance from the exterior end surface that is smaller than or equal to the pre-determined distance (A); and
   wherein the receiving part further comprising an undercut on an inner surface of the legs adjacent to the first internal thread, the undercut extends in a circumferential direction and the first internal thread extending to the undercut, the undercut having an edge farthest away from the first internal thread, the edge being located at a third distance (B) from the exterior end surface, the distance (B) being larger than the predetermined distance (A);
   wherein the first external thread of the securing element is movable into the undercut.

20. The anchoring element of claim 19 wherein the first internal thread of the receiving part comprises fewer than four full turns.

* * * * *